United States Patent [19]

Freebersyser

[11] Patent Number: 5,306,507
[45] Date of Patent: Apr. 26, 1994

[54] PROCESS AND COMPOSITION CONTAINING PAMABROM AND PYRILAMINE MALEATE

[75] Inventor: Steven R. Freebersyser, St. Louis County, Mo.

[73] Assignee: Mallinckrodt Specialty Chemicals Company, Chesterfield, Mo.

[21] Appl. No.: 857,822

[22] Filed: Mar. 26, 1992

[51] Int. Cl.$^5$ .............................................. A61K 9/16
[52] U.S. Cl. .................................... 424/493; 424/490
[58] Field of Search ................ 424/490, 493; 514/576, 514/783

[56] References Cited

U.S. PATENT DOCUMENTS

| | | | |
|---|---|---|---|
| 2,502,151 | 3/1950 | Horclois | 544/330 |
| 2,711,411 | 6/1955 | Holbert | 544/271 |
| 2,998,450 | 8/1961 | Wilbert | 564/141 |
| 5,011,688 | 4/1991 | Calam | 514/783 |
| 5,037,823 | 8/1991 | Jones | 514/576 |
| 5,085,868 | 2/1992 | Mattsson | 424/490 |

OTHER PUBLICATIONS

Merck Index, Entry No. 6865, 10th Ed., p. 1005 (1983).
Merck Index, Entry No. 7883, 10th Ed., p. 1152 (1983).
Merck Index, Entry No. 39, 10th Ed., p. 7 (1983).

*Primary Examiner*—Thurman K. Page
*Assistant Examiner*—W. Benston
*Attorney, Agent, or Firm*—Rothwell, Figg, Ernst & Kurz

[57] ABSTRACT

A product and process for preparing a pharmaceutical composition for forming tablets, the composition containing pamabrom and pyrilamine maleate. In preferred embodiments, the composition also contains acetaminophen. A fluid bed granulator is charged with a first material containing pamabrom or pyrilamine maleate, and a first liquid containing pregelatinized starch is sprayed onto the first material so as to form a barrier coat. The barrier coated material is dried and then further coated with a second liquid containing only one of pamabrom and pyrilamine maleate, whichever was not present in the first material charged to the fluid bed granulator. The further coated material is then dried to a moisture content of from about 0.5% to less than about 2% by weight, so as to form particles in which the pamabrom and pyrilamine maleate are separated by the pregelatinized starch barrier.

8 Claims, No Drawings

PROCESS AND COMPOSITION CONTAINING PAMABROM AND PYRILAMINE MALEATE

BACKGROUND OF THE INVENTION

1. Field of the Invention

The present invention relates to the field of pharmaceutical compositions, particularly to a process and composition containing pamabrom and pyrilamine maleate.

2. Description of the Background Art

Many pharmaceutical compositions contain a combination of ingredients. Different compounds can be combined into a single pharmaceutical formulation so as to enhance the effectiveness of one or more of the compounds. Alternatively, a pharmaceutical composition can contain different compounds for treatment of a variety of symptoms.

Pamabrom is a diuretic, and is described in expired U.S. Pat. No. 2,711,411. Pamabrom is a fine white powder which decomposes at about 300° C., and has a solubility in water of greater than 30 g/100 ml at 25° C. A saturated aqueous solution of pamabrom has a pH of from about 8.0 to 8.5. Merck Index, entry no. 6865, 10th ed., p 1005 (1983).

Pyrilamine is an antihistaminic pharmaceutical which is described in expired U.S. Pat. No. 2,502,151. Pyrilamine maleate forms crystals which are stable in air, having a melting point of about 100°-101° C. One gram of pyrilamine maleate dissolves in about 0.4 ml water and a 10% solution thereof has a pH of about 5.1. Pyrilamine maleate can precipitate to the oily, free base at a pH of 7.5-8.0. Merck Index, supra. entry no. 7883, p. 1152.

Acetaminophen is an analgesic and antipyretic described in expired U.S. Pat. No. 2,998,450. Acetaminophen forms large monoclinic prisms from water, and has a melting point of about 169°-170.5° C. Acetaminophen is very slightly soluble in cold water and considerably more soluble in hot water. Merck Index, supra, entry no. 39, p. 7. Acetaminophen is one of the most widely used over-the-counter analgesics, and it is highly desirable to form pharmaceutical compositions containing acetaminophen and other pharmaceutical compounds.

In view of the diuretic activity of pamabrom and the antihistaminic activity of pyrilamine maleate, it would be desirable to combine these compounds in certain pharmaceutical compositions. Furthermore, because of the analgesic and antipyretic activities of acetaminophen, it would be desirable to combine acetaminophen with pamabrom and pyrilamine maleate in a single pharmaceutical composition.

Additionally, in view of the threat of product tampering, it is highly desirable to be able to form tablets from pharmaceutical compositions containing more than one active ingredient.

One method of manufacturing pharmaceutical compositions containing two or more active ingredients is to prepare separate formulations containing the respective active ingredients, and then dry blending the formulations together to achieve the desired active ingredient levels. However, from a processing standpoint, it is often more desirable to produce one formulation containing all active ingredients utilizing a single process.

There thus remains a need in the art for tablettable pharmaceutical compositions containing more than one active ingredient.

SUMMARY OF THE INVENTION

In accordance with the present invention, a process is disclosed for preparing a pharmaceutical composition which can be formed into tablets, and which contains pamabrom and pyrilamine maleate. In the inventive process, a fluid bed granulator is charged with a first material so as to form a fluidized bed of the first material. The first material comprises at least one pharmaceutical, said at least one pharmaceutical comprising only one member selected from the group consisting of pamabrom and pyrilamine maleate. A first liquid containing pregelatinized starch is sprayed onto the fluidized bed of the first material, so as to form a barrier coat on the first material with the pregelatinized starch. The coated material is dried in the granulator to a moisture content of less than about 2% by weight. The dried material then is further coated with a second liquid containing the other member of the group consisting of pamabrom and pyrilamine maleate which was not in the first material charged to the fluid bed granulator. The further coated material then is dried to a moisture content from about 0.5% to less than about 2% by weight.

A pharmaceutical composition in accordance with the present invention comprises particles having a core containing only one member of the group consisting of pamabrom and pyrilamine maleate. The particles have an intermediate coating containing pregelatinized starch and an outer coating containing the other member of said group which is not present in the core. The intermediate coating thereby separates the core from the outer coating, so as to separate the pamabrom from the pyrilamine maleate.

DETAILED DESCRIPTION OF THE PREFERRED EMBODIMENTS

The present invention arose in connection with the desire to produce a single tablettable formulation containing both pamabrom and pyrilamine maleate. The single formulation also desirably contains acetaminophen as an active ingredient. The goal was to produce a single formulation capable of being formed into tablets using conventional tabletting machines.

In accordance with one embodiment, desirable formulations contain an amount of pamabrom within the range of about 2-6% by weight, pyrilamine maleate within the range of about 1.5-3.5% by weight and acetaminophen within the range of about 75-85% by weight. The remainder of the formulation is made up of inactive ingredients and excipients such as binders, disintegrents, lubricants, fillers and the like, which are normally utilized to form tablettable compositions.

Suitable binders include polyvinylpyrrolidones such as Povidone K-90 ®, partially gelatinized starches such as Starch 1500 ®, ethylcellulose, hydroxypropylmethylcellulose, gelatin, maltodextrin, hydroxypropylcellulose, and the like.

Suitable disintegrents include Crospovidone ®, corn starch, microcrystalline cellulose, Explotab ® (Emco 65), and the like.

Suitable lubricants include stearic acid, magnesium stearate and the like.

Suitable fillers include calcium phosphate dibasic, lactose and the like.

During initial attempts to produce tablettable formulations using a fluid bed granulator, the active ingredients set forth above, namely pamabrom, pyrilamine maleate and acetaminophen were mixed together with excipients including binder and disintegrant, and the mixture was charged to a fluid bed granulator. Onto this mixture was added a granulating solution containing binder dissolved in water. Following fluid bed granulation, lubricants were blended with the granulation and the granulation was tabletted using conventional tabletting equipment. Mottling (dark spots) were observed on the faces and sides of the tablets. Without being bound to any particular theory, it is believed that the mottling was a result of an interaction between the pamabrom and the pyrilamine maleate during granulation.

Process modifications were made in an attempt to eliminate mottling. Two of the active ingredients, pyrilamine maleate and acetaminophen, along with minor excipients including binder and disintegrant, were granulated in a fluidized bed with 60% of the granulation solution previously utilized. A higher atomization pressure was used so that a finer particle size granulation would be made. After the addition was complete, the material was dried. Then, the pamabrom was added to the granulation and granulated with the other 40% of the granulation solution. After drying, lubricants were blended with the granulation and the material was tabletted using conventional tabletting machines. Mottling was still observed on the tablets.

The present invention provides a process that eliminates the mottling of tablets which was observed when utilizing the previously described fluid bed granulation processes.

In the inventive process, a fluid bed granulator is initially charged with a first material containing only one member selected from the group consisting of pamabrom and pyrilamine maleate.

In preferred embodiments, the first material contains pamabrom, and pyrilamine maleate is left out of the first material.

In particularly preferred embodiments, the first material charged to the fluid bed granulator also contains acetaminophen, in addition to pamabrom. In particularly preferred embodiments, the first material charged to the fluid bed granulator also contains minor amounts of excipients including a first binder and a disintegrant. Particularly preferred excipients include Starch 1500 ®, Crospovidone ®, and Explotab ® (Emco 65).

Onto the fluidized bed of first material is sprayed a first liquid containing a pregelatinized starch, such at Starch 1551 ®, so as to form a barrier coat on the first material with the pregelatinized starch. In particularly preferred embodiments, the pregelatinized starch is substantially completely gelatinized starch. Substantially completely gelatinized starch can be prepared by pregelatinizing starch using a high shear mixture so as to form the gelatinized starch with which the liquid containing gelatinized starch is made. In particularly preferred embodiments, the gelatinized starch is present in an aqueous liquid.

In preferred embodiments, the moisture content of the fluidized bed granulation during formation of the gelatinized starch barrier coat is maintained at about 15% by weight or less. In more preferred embodiments, the moisture content of the granulation during formation of the barrier coat is maintained between about 1% and 15% by weight, most preferably at from about 5% to about 10% by weight.

The barrier coated granulation then is dried in the granulator to a moisture content of less than about 2% by weight, preferably to a moisture content of about 1% by weight.

After drying, the granulation is further coated with a second liquid containing the other member of the group consisting of pamabrom and pyrilamine maleate which was not present in the first material charged to the fluid bed granulator. When the first material charged to the fluid bed granulator contains pamabrom, the second liquid which later is sprayed onto the dried, starch-coated granulation contains pyrilamine maleate.

In preferred embodiments, the second liquid containing pyrilamine maleate is an aqueous solution of pyrilamine maleate. In particularly preferred embodiments, the aqueous solution containing pyrilamine maleate further contains a second binder such as a polyvinylpyrrolidone (e.g., povidone K-90 ® and/or maltodextrin).

The granulation thus coated with pyrilamine maleate then is dried to a moisture contents of from about 0.5% by weight to less than about 2% by weight, more preferably to a moisture content of from about 0.5% by weight to about 1.4% by weight.

The thus produced dried granulation contains cores of acetaminophen and pamabrom coated with pregelatinized starch, and further coated with pyrilamine maleate. This granulation then can be dry blended with one or more lubricants such as stearic acid and magnesium stearate, to form a directly tablettable formulation.

The invention is further illustrated by the following examples, which are not intended to be limiting:

Example I

A barrier coat solution was prepared by heating 370 ml of water to almost boiling and adding 30 g Starch 1551 ® while mixing in a Brookfield mixer for 5 minutes. The barrier coat solution then was kept hot on a hot plate while an outer coat solution was prepared by dissolving 10 g Povidone K-90 ® and 25.2 g pyrilamine maleate in 200 ml of water.

To a STREA-1 Aeromatic AG fluid bed granulator was charged 800 g acetaminophen, 40 g pamabrom, 31 g Starch 1500 ®, 30.8 g Crospovidone and 25 g Explotab ® (Emco 65). The inlet temperature of the fluid bed granulator unit was set to 60° C., and the bed outlet was allowed to heat up to 36° C. The pump of the Aeromatic AG unit was set at setting 1, atomization air pressure at 2.5 bar and the top hole was nozzled. Spraying of the barrier coat solution onto the material in the granulator was commenced at time 0, and 3 minutes later, the outlet temperature of the granulator was 32° C. Ten minutes after spraying commenced, the pump feed was reduced to 0.7 and spraying of the barrier coat solution was complete after 18 minutes. The moisture content of the coated granulation was 6.77% by weight.

The nozzle of the Aeromatic AG fluid bed unit then was removed and the granulation was dried for 5 minutes at an inlet temperature of 50° C and an outlet temperature of 30° C, to a granulation moisture content of 1.67% by weight. The granulation then was dried an additional 30 seconds to a moisture content of 1.18% by weight.

The bed then was heated for 4 minutes at a 50° C. inlet temperature, and the above-described pyrilamine maleate solution was sprayed onto the barrier coated granulation at 4 bar with a pump setting of 0.5 and an inlet temperature of 50° C., an outlet temperature of 32° C., and a nozzled top hole of the Aeromatic AG unit.

Spraying of the pyrilamine maleate solution was completed after 20 minutes, with an outlet temperature of 32° C. The moisture content of the granulation then was 1.32% by weight.

The nozzle of the Aeromatic AG unit then was removed, and the granulation was dried for 2 minutes at 40° C. inlet temperature and 32° C. outlet temperature. The moisture content of the granulation then was 0.77% by weight.

To 769 g of the thus prepared granulation was added two lubricants, namely 3.07 g stearic acid and 3.06 g magnesium stearate. The lubricants were blended with the granulation for 10 minutes in a twin shell blender, and the granulation was tabletted using conventional tabletting equipment. No mottling was observed with the thus-formed tablets.

Example II

The procedures of Example I were substantially repeated, except the barrier coat solution was made using 400 ml of water and the pyrilamine maleate/polyvinylpyrrolidone solution was made up in 250 ml of water. No mottling was observed in tablets produced with this formulation.

Example III

The procedures of Example I were substantially repeated, except that the Povidone K-90 ® was replaced with 10 g maltodextrin (Maltrin M100 ®). No mottling was observed in tablets produced according to this process.

The present invention provides an effective way to eliminate the mottling problem previously experienced with formulations containing both pamabrom and pyrilamine maleate.

What is claimed is:

1. A pharmaceutical composition comprising particles having a core containing only one member selected from the group consisting of pamabrom and pyrilamine maleate, which particles have a solid intermediate layer containing pregelatinized starch, and an outer coating containing the other member of said group consisting of pamabrom and pyrilamine maleate which is not present in said core, which member present in said core is not present in said outer coating, wherein said solid intermediate starch-containing layer separates said core containing one said member from said outer coating containing the other said member, so as to separate said pamabrom from said pyrilamine maleate.

2. The composition of claim 1 wherein said core contains pamabrom and said outer coating contains pyrilamine maleate.

3. The composition of claim 2 wherein said core further contains acetaminophen intermixed with said pamabrom.

4. The composition of claim 3 wherein said core further contains a disintegrent and a binder.

5. The composition of claim 4 wherein said outer coating further contains binder.

6. The composition of claim 5 having a moisture content of from about 0.5% to about 1.4% by weight.

7. The composition of claim 6 further comprising a lubricant blended with said particles.

8. The composition of claim 6, comprising pamabrom at a concentration within the range of about 2–6% by weight, pyrilamine maleate at a concentration within the range of about 1.5–3.5% by weight, acetaminophen at a concentration within a range of about 75–85% by weight, and gelatinized starch at a concentration within the range of about 2–4% by weight, the remainder of said composition comprising binder and disintegrent.

* * * * *